(12) United States Patent
Kim et al.

(10) Patent No.: US 12,016,897 B2
(45) Date of Patent: Jun. 25, 2024

(54) MICROPARTICLES CONTAINING LEUPROLIDE AND METHOD FOR PRODUCING THE SAME

(71) Applicant: INVENTAGE LAB INC., Seongnam-si (KR)

(72) Inventors: Ju Hee Kim, Seongnam-si (KR); Min Sung Kim, Seongnam-si (KR)

(73) Assignee: INVENTAGE LAB INC., Seongnam-si (KR)

( * ) Notice: Subject to any disclaimer, the term of this patent is extended or adjusted under 35 U.S.C. 154(b) by 115 days.

(21) Appl. No.: 17/832,229

(22) Filed: Jun. 3, 2022

(65) Prior Publication Data

US 2023/0173015 A1   Jun. 8, 2023

(30) Foreign Application Priority Data

Dec. 3, 2021   (KR) .......................... 10-2021-0171567

(51) Int. Cl.
*A61K 9/16* (2006.01)
*A61K 38/09* (2006.01)

(52) U.S. Cl.
CPC ............ *A61K 38/09* (2013.01); *A61K 9/1647* (2013.01); *A61K 9/1694* (2013.01)

(58) Field of Classification Search
None
See application file for complete search history.

(56) References Cited

U.S. PATENT DOCUMENTS

2016/0228494 A1* 8/2016 Schwach ............. A61K 9/1647

FOREIGN PATENT DOCUMENTS

| CN | 113081959 A | 7/2021 | |
|---|---|---|---|
| KR | 20030064401 A | 7/2003 | |
| KR | 101039237 B1 | 6/2011 | |
| KR | 102157124 B1 | 9/2020 | |
| KR | 102259589 B1 | 6/2021 | |
| KR | 102386163 B1 | 4/2022 | |
| TW | 201601744 A | 1/2016 | |
| TW | 201834640 A | 10/2018 | |
| WO | WO-0110414 A1 * | 2/2001 | ............. A61K 38/09 |

OTHER PUBLICATIONS

Paarakh et al. "Release Kinetics-Concepts and Applications"; International Journal of Pharmacy Research & Technology; vol. 8, pp. 12-20. (Year: 2018).*
Soumya Ranjan Satapathy et al, Development and Characterization of Leuprolide Acetate Encapsulated PLGA Microspheres for Parenteral Controlled Release Depot Injection, Indian Journal of Pharmaceutical Education and Research, Jan.-Mar. 2021, vol. 55, Issue 1, pp. 107-116, Association of Pharmaceutical Teachers of India, Karnataka, India.
International search report of PCT/KR2022/018982, Mar. 6, 2023.

* cited by examiner

*Primary Examiner* — Susan T Tran
(74) *Attorney, Agent, or Firm* — STIP Law Group, LLC (57) ABSTRACT

The present invention provides microparticles containing leuprolide and a method for producing the same. When the microparticles are administered by injection, they may lower pain due to their small size, control the release rate of leuprolide at a target site, prevent excessive release of leuprolide at an initial stage, enable exposure to a sufficient amount of the drug to exhibit the effect of leuprolide, and exhibit the effect of leuprolide for 1 month or more. The present invention also provides a method for producing microparticles, in which the microparticles have a uniform particle size and a smooth surface and may exhibit the effect of releasing leuprolide sustainably over a long period of time.

7 Claims, 6 Drawing Sheets

MICROPARTICLES CONTAINING LEUPROLIDE AND METHOD FOR PRODUCING THE SAME

CROSS-REFERENCE TO RELATED APPLICATIONS

This application claims the priority of the Korean Patent Applications NO 10-2021-0171567, filed on Dec. 3, 2021, in the Korean Intellectual Property Office, the disclosure of which is incorporated herein by reference.

BACKGROUND

1. Technical Field

The present invention relates to microparticles containing leuprolide and a method for producing the same.

2. Related Art

Luteinizing hormone releasing hormone (LHRH), also known as gonadotropin releasing hormone (GnRH), is hypothalamic decapeptide (pGlu-His-Trp-Ser-Tyr-Gly-Leu-Arg-Pro-Gly-NH2) that controls the reproductive system of vertebrates.

LHRH is released into the capillaries of the hypothalamic-pituitary portal system of the median eminence and the infundibular stalk. LHRH reaches the anterior pituitary gland by this capillary network and reaches the gonadal stimulated target cells by the second capillary network. GnRH acts at the membrane level of target cells through receptors with seven transmembrane segments that are coupled to phospholipase C via G proteins to increase intracellular calcium flux.

This action induces the biosynthesis and release of the gonadotropin FSH (follicle-stimulating hormone) and LH (luteinizing hormone). It has been found that LHRH agonists and antagonists are effective for the treatment of female endometriosis, fibroids, polycystic ovarian syndrome, breast cancer, ovarian cancer, endometrial cancer, gonadotropin-induced pituitary desensitization during a medically assisted delivery protocol, male benign prostate enlargement and polymorphism and prostate cancer, and male or female precocious puberty.

Currently used LHRH (luteinizing hormone-releasing hormone) agonists are generally peptide compounds that are required to be administered via intravenous or subcutaneous routes due to their low oral bioavailability.

In addition, LHRH agonists are drugs for chronic diseases that should be taken for a long period of time. For drugs of the LHRH agonist group, it is known that rapid exposure to sufficient amounts of the drugs at an initial stage is required in order to exhibit their therapeutic effects.

One of the LHRH agonists, leuprolide acetate, has a drawback in that it has a short half-life upon conventional subcutaneous or intramuscular injection, and thus it disappears within a few hours due to a rapid decrease in the blood concentration thereof after administration. For this reason, leuprolide acetate has the inconvenience of having to be administered every day in order to maintain the medicinal effect thereof, and in particular, this inconvenience is further exacerbated because it is administered by injection.

In order to overcome this drawback, formulations (i.e. sustained release formulations) whose effect lasts for 4 weeks or more after single administration have been developed and sold.

However, it is known that exposure of a target site to a sufficient amount of leuprolide acetate at the initial stage of administration is required to exhibit the effect of the drug. In addition, it is known that leuprolide acetate inhibits circulating sex hormone levels for 2 to 4 weeks after an initial rise in the blood concentration thereof, and thus it is desirable that the initial release rate of leuprolide acetate from microparticles containing the same is high in order for leuprolide to be effective.

Therefore, it is known that all products currently distributed in the market show excessive release of leuprolide at an initial stage when the blood concentration of leuprolide is measured after administration by injection, and that when excessive release of leuprolide at the initial stage does not appear, the effect of leuprolide is not exhibited.

PRIOR ART DOCUMENTS

Patent Documents (Patent Document 1) KR 10-2003-0064401 A1

SUMMARY

An object of the present invention is to provide microparticles containing leuprolide and a method for producing the same.

Another object of the present invention is to provide microparticles containing leuprolide, which, when administered by injection, may lower pain due to their small size, control the release rate of leuprolide at a target site, prevent excessive release at an initial stage, enable exposure to a sufficient amount of the drug to exhibit the effect of leuprolide, and exhibit the effect of leuprolide for 1 month or more.

Still another object of the present invention is to provide a method for producing microparticles, in which the microparticles have a uniform particle size and a smooth surface and may exhibit the effect of releasing leuprolide sustainably over a long period of time.

To achieve the above objects, microparticles containing leuprolide according to one embodiment of the present invention contain leuprolide and a biodegradable polymer, and have an average diameter of 40 to 100 μm and a value of 0.5 to 2 as determined by the following Equation 1:

$$\frac{D90 - D50}{D50 - D10} \qquad \text{[Equation 1]}$$

wherein D10 is a particle diameter corresponding to 10% cumulative (from 0 to 100%) undersize particle size distribution, D50 is a particle diameter corresponding to 50% cumulative (from 0 to 100%) undersize particle size distribution, and D90 is a particle diameter corresponding to 90% cumulative (from 0 to 100%) undersize particle size distribution.

The leuprolide and the biodegradable polymer may be contained in a weight ratio of 1:2 to 1:10.

When the microparticles are administered by injection, the release rate of leuprolide at a target site may be controlled, and thus the problem of excessive release of leuprolide at an initial stage may be eliminated and the testosterone inhibitory effect of leuprolide may last for one month or more.

The microparticles may have a value of 1 to 15 as determined by the following Equation 2, which represents the plasma concentration of leuprolide measured after administering the microparticles containing leuprolide to a beagle dog by injection at a single dose of leuprolide acetate of 11.25 mg:

$$\frac{C_{max}}{C_{24h}} \quad \text{[Equation 2]}$$

wherein $C_{max}$ is the maximum plasma concentration of leuprolide for 24 hours after administration by injection; and $C_{24\ h}$ is the plasma concentration value of leuprolide in blood collected 24 hours after administration by injection.

A method for producing microparticles containing leuprolide according to another embodiment of the present invention may include steps of: 1) preparing a first mixture by mixing leuprolide and a biodegradable polymer; 2) preparing a second mixture by dissolving a surfactant in a solvent; 3) injecting the first mixture and the second mixture into a first microchannel and a second microchannel, respectively, which have an intersection formed therebetween, and allowing the first mixture and the second mixture to flow, thereby producing microparticles at the intersection; 4) collecting the microparticles in a bath containing the second mixture; 5) removing an organic solvent from the collected microparticles; and 6) washing the microparticles, from which the organic solvent has been removed, with purified water, followed by freeze drying, wherein the microparticles may have a value of 0.5 to 2 as determined by the following Equation 1:

$$\frac{D90 - D50}{D50 - D10} \quad \text{[Equation 1]}$$

wherein D10 is a particle diameter corresponding to 10% cumulative (from 0 to 100%) undersize particle size distribution, D50 is a particle diameter corresponding to 50% cumulative (from 0 to 100%) undersize particle size distribution, and D90 is a particle diameter corresponding to 90% cumulative (from 0 to 100%) undersize particle size distribution.

The first mixture may be injected into the first microchannel under a pressure of 700 to 1,300 mbar, and the pressure may be increased at a first rate of 10 to 30 mbar/min, and when the pressure reaches 950 to 1,500 mbar, it may be increased at a second rate of 2 to 8 mbar/min.

The second mixture may be injected into the second microchannel under a pressure which is 2 to 4 times higher than the pressure under which the first mixture is injected into the first microchannel.

Step 5) may include steps of: 5-1) subjecting the microparticles to first stirring at a speed of 100 to 300 rpm at 15 to 20° C. for 20 to 40 minutes; 5-2) subjecting the microparticles to second stirring at a speed of 100 to 300 rpm at 30 to 40° C. for 60 to 120 minutes; and 5-3) subjecting the microparticles to third stirring at a speed of 100 to 300 rpm at 40 to 45° C. for 4 to 8 hours.

Effects of the Invention

The present invention provides microparticles containing leuprolide, which, when administered by injection, may lower pain due to their small size, control the release rate of leuprolide at a target site, prevent excessive release of leuprolide at an initial stage, enable exposure to a sufficient amount of the drug to exhibit the effect of leuprolide, and exhibit the effect of leuprolide for 1 month or more.

The present invention also provides a method for producing microparticles, in which the microparticles have a uniform particle size and a smooth surface and may exhibit the effect of releasing leuprolide sustainably over a long period of time.

DETAILED DESCRIPTION

Hereinafter, embodiments of the present invention will be described in detail so that those of ordinary skill in the art to which the present invention pertains can easily carry out the present invention. However, the present invention may be embodied in a variety of different forms and is not limited to the embodiments described herein.

As used herein, the term "leuprolide" may include both 5-oxo-L-prolyl-Lhistidyl-L-tryptophanyl-L-seryl-L-tyrosyl-D-leucyl-L-leucyl-L-arginyl-L-prolyl ethylamide and pharmaceutically acceptable salts thereof. Leuprolide may be expressed as leuprorelin, and leuprolide and pharmaceutically acceptable salts thereof may all be used regardless of expression.

As used herein, the term "pharmaceutically acceptable" refers to a salt which is physiologically acceptable and, when administered to the human beings, generally does not cause allergic reactions or similar reactions.

As used herein, the term "pharmaceutically acceptable salt" refers to an acid addition salt formed by a pharmaceutically acceptable free acid. As the free acids, an organic acid and an inorganic acid may be used. Examples of the organic acid include, but are not limited to, citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluenesulfonic acid, glutamic acid, and aspartic acid. In addition, examples of the inorganic acid include, but are not limited to, hydrochloric acid, hydrobromic acid, sulfuric acid, and phosphoric acid.

To achieve the above objects, microparticles containing leuprolide according to one embodiment of the present invention contain leuprolide and a biodegradable polymer, and have an average diameter of 40 to 100 µm and a value of 0.5 to 2 as determined by the following Equation 1:

$$\frac{D90 - D50}{D50 - D10} \quad \text{[Equation 1]}$$

wherein D10 is a particle diameter corresponding to 10% cumulative (from 0 to 100%) undersize particle size distribution, D50 is a particle diameter corresponding to 50% cumulative (from 0 to 100%) undersize particle size distribution, and D90 is a particle diameter corresponding to 90% cumulative (from 0 to 100%) undersize particle size distribution.

The terms "D10", "D50" and "D90" respectively refer to diameter values corresponding to 10%, 50% and 90% cumulative (from 0 to 100%) undersize particle size distribution of the microparticles.

Equation 1 above defines not only the average diameter of the microparticles of the present invention, but also the ratio of (D90-D50) to (D50-D10), which is the ratio of the difference between 90% cumulative undersize particle size distribution and 50% cumulative undersize particle size distribution to the difference between 50% cumulative undersize particle size distribution and 10% cumulative undersize particle size distribution in the average particle size distribution. Equation 1 above indicates the uniformity of the particle distribution, and a value closer to 1, as determined by Equation 1 above, indicates a more uniform particle size distribution.

Equation 1 of the present invention is used to more clearly confirm the size distribution of the microparticles, and the value determined by Equation 1 may be 0.5 to 2, 0.7 to 1.5, or 0.9 to 1.3. When the value determined by Equation 1 is satisfied and the average diameter of the microparticles is 40 to 100 µm, it means that the microparticles have a size distribution close to the average diameter value. In this case, microparticles having a uniform size may be administered into the body by injection, and may be biodegraded at similar rates, and the biodegradation of the microparticles may exhibit the effect of releasing leuprolide.

That is, for the microparticles containing leuprolide, the release rate of leuprolide release in the body is highly correlated with the size and specific surface area of the particles, and it is essential to use microparticles having a uniform diameter in order to increase the specific surface area. When microparticles having a very uniform particle size distribution as described above are used and injected into the body, they may prevent excessive release of leuprolide at an initial stage and exhibit the effect of releasing leuprolide continuously over a long period of time, thereby exhibiting the effect of leuprolide for 1 month or more.

The leuprolide and the biodegradable polymer may be contained at a weight ratio of 1:2 to 1:10, preferably 1:2 to 1:8, more preferably 1:4 to 1:7. When they are contained at a weight ratio within the above range, biodegradation of the biodegradable polymer may exhibit the effect of releasing leuprolide sustainably over a long period of time.

The biodegradable polymer may be selected from the group consisting of polylactic acid, polylactide, polylactic-co-glycolic acid, polylactide-co-glycolide (PLGA), polyphosphazene, polyiminocarbonate, polyphosphoester, polyanhydride, polyorthoester, polycaprolactone, polyhydroxyvalerate, polyhydroxybutyrate, polyamino acids, and mixtures thereof, with polylactide-co-glycolide (PLGA) or polylactide being preferred, without being limited thereto.

The microparticles containing leuprolide according to another embodiment of the present invention may have a value of 1 to 15 as determined by the following Equation 2, which represents the plasma concentration of leuprolide measured after administering the microparticles containing leuprolide to a beagle dog by injection at a single dose of leuprolide acetate of 11.25 mg:

$$\frac{C_{max}}{C_{24h}} \quad \text{[Equation 2]}$$

wherein $C_{max}$ is the maximum plasma concentration of leuprolide for 24 hours after administration by injection; and $C_{24\ h}$ is the plasma concentration value of leuprolide in blood collected 24 hours after administration by injection.

As described above, it is known that excessive release of leuprolide at an initial stage is essential for exerting the medicinal effect of leuprolide. That is, the release rate of leuprolide at an initial stage was required to be high so that the plasma concentration of leuprolide after administration by injection would be high at an initial stage. That is, it is known that the release rate of leuprolide at an initial stage should be at a high level in order to exhibit a sufficient pharmacological effect as an LHRH agonist. For this reason, leuprolide formulations distributed in the market have been prepared so that the release rate of the drug at an initial stage can be high.

In this regard, not only leuprolide but also most drugs may cause side effects upon excessive exposure to these drugs. That is, side effects such as nausea, pain around the injection site, headache, urination disorder, and joint pain may occur due to excessive release of leuprolide.

It is known that, despite the presence of concerns about the occurrence of the above-described side effects, excessive release of leuprolide at an initial stage after administration by injection is required in order to exhibit the efficacy of leuprolide.

In contrast, in the present invention, when the value determined by Equation 2 is satisfied, the maximum plasma concentration value of leuprolide within 24 hours may be lowered compared to those of conventional leuprolide formulations, and the effect of releasing leuprolide sustainably over a long period of time may be exhibited.

That is, as a result of conducting the same experiment on a purchased commercially available product to determine the value of Equation 2, it could be confirmed that the commercially available product exhibited a high value of 50 to 60, whereas administration of the microparticles of the present invention exhibited a value of 1 to 15, preferably 2 to 10, more preferably 3 to 8, which did significantly differ from the value of the commercially available product.

Regarding the difference between the above results, the numerator value of Equation 2 for the conventional leuprolide formulation was high because excessive release of leuprolide at an initial stage is known to be necessarily required to exert the effect of leuprolide, whereas the microparticles of the present invention exhibited the optimal plasma concentration of leuprolide that can prevent expressive release of leuprolide at an initial stage and, at the same time, exert the effect of leuprolide by releasing leuprolide sustainably over a long period of time.

Since the numerator of Equation 2 includes the maximum plasma concentration value of leuprolide, the value of Equation 2 may increase as the maximum plasma concentration value increases. Conversely, when the value of $C_{24\,h}$ as the denominator is small, the value of Equation 2 may increase.

The fact that the value of Equation 2 increases as the maximum plasma concentration value of leuprolide increases means that excessive release at an initial stage occurs after administration by injection. In addition, the fact that the value of Equation 2 increases as the $C_{24\,h}$ value is small means that the effect of releasing the drug for a long period of time is not exhibited.

Accordingly, when the value of Equation 2 is included within the scope of the present invention, excessive release of leuprolide at an initial stage may be prevented, the medicinal effect of leuprolide may be exerted, and the medicinal effect of leuprolide may be exerted sustainably for 1 month or more after administration by injection.

A method for producing microparticles containing leuprolide according to another embodiment of the present invention may include steps of: 1) preparing a first mixture by mixing leuprolide and a biodegradable polymer; 2) preparing a second mixture by dissolving a surfactant in solvent; 3) injecting the first mixture and the second mixture into a first microchannel and a second microchannel, respectively, which have an intersection formed therebetween, and allowing the first mixture and the second mixture to flow, thereby producing microparticles at the intersection; 4) collecting the microparticles in a bath containing the second mixture; 5) removing the organic solvent from the collected microparticles; and 6) washing the microparticles, from which the organic solvent has been removed, with purified water, followed by freeze drying, wherein the microparticles may have a value of 0.5 to 2 as determined by the following Equation 1:

$$\frac{D90 - D50}{D50 - D10} \quad \text{[Equation 1]}$$

wherein D10 is a particle diameter corresponding to 10% cumulative (from 0 to 100%) undersize particle size distribution, D50 is a particle diameter corresponding to 50% cumulative (from 0 to 100%) undersize particle size distribution, and D90 is a particle diameter corresponding to 90% cumulative (from 0 to 100%) undersize particle size distribution.

Step 1) is a step of preparing a first mixture by mixing leuprolide and a biodegradable polymer in an organic solvent, wherein the biodegradable polymer is selected from the group consisting of polylactic acid, polylactide, polylactic-co-glycolic acid, polylactide-co-glycolide (PLGA), polyphosphazene, polyiminocarbonate, polyphosphoester, polyanhydride, polyorthoester, polycaprolactone, polyhydroxyvalerate, polyhydroxybutyrate, polyamino acids, and mixtures thereof, with polylactide-co-glycolide (PLGA) being preferred, without being limited thereto.

In addition, the organic solvent is water-immiscible, and may be, for example, any one or more selected from the group consisting of chloroform, chloroethane, dichloroethane, trichloroethane, and mixtures thereof, with dichloromethane being preferred, without being limited thereto. In addition to the above-listed organic solvents, any organic solvent may be used without limitation, as long as it is capable of dissolving the biodegradable polymer and leuprolide and may be easily selected by those skilled in the art.

Step 1) is a step of preparing a first mixture by mixing leuprolide and a biodegradable polymer, and as the solvent, the organic solvent described above is used. The organic solvent is used to completely dissolve leuprolide and the biodegradable polymer based on the dissolution properties thereof.

More specifically, leuprolide acetate is dissolved in a first solvent, and the biodegradable polymer is dissolved in a second solvent. Then, the leuprolide acetate dissolved in the first solvent and the biodegradable polymer dissolved in the second solvent are mixed together to obtain a first mixture.

The first mixture contains leuprolide and the biodegradable polymer at a weight ratio of 1:2 to 1:10, preferably 1:2 to 1:8, more preferably 1:4 to 1:7. If the weight ratio between leuprolide and the biodegradable polymer is less than 1:2, that is, if the content of the biodegradable polymer is lower than the lower limit of the above weight ratio, a problem may arise in that, because the content of the biodegradable polymer is lower than the content of leuprolide, it is difficult to produce sustained-release particles in which leuprolide is uniformly distributed in spherical biodegradable polymer particles. If the weight ratio between leuprolide and the biodegradable polymer is more than 1:10, that is, if the content of the biodegradable polymer is higher than the upper limit of the above weight ratio, a problem may arise in that, because the content of leuprolide in the sustained-release particles is low, a large amount of sustained-release particles need to be administered in order to administer the drug at a desired concentration.

More specifically, the content of the biodegradable polymer in the first mixture is 15 to 25 wt %, preferably 20 wt %, without being limited thereto.

Step 2) is a step of preparing a second mixture by dissolving a surfactant in water. As the surfactant, any surfactant may be without limitation as long as it may help the biodegradable polymer solution to form a stable emulsion. Specifically, the surfactant may be any one or more selected from the group consisting of nonionic surfactants, anionic surfactants, cationic surfactants, and mixtures thereof, and more specifically, may be any one or more selected from the group consisting of methylcellulose, polyvinylpyrrolidone, lecithin, gelatin, polyvinyl alcohol, polyoxyethylene sorbitan fatty acid ester, polyoxyethylene castor oil derivatives, sodium lauryl sulfate, sodium stearate, ester amine, linear diamine, fatty amines, and mixtures thereof, with polyvinyl alcohol being preferred, but the surfactant is not limited to the above examples.

Step 3) is a step of injecting the first mixture and the second mixture into microchannels formed on a wafer and allowing the first mixture and the second mixture to flow.

More specifically, the microchannels may be formed on a material selected from the group consisting of a silicon wafer and a polymer film, but the material is not limited to the above examples, and it is possible to use any material on which the microchannels may be formed.

The polymer film may be selected from the group consisting of polyimide, polyethylene, fluorinated ethylene propylene, polypropylene, polyethylene terephthalate, polyethylene naphthalate, polysulfone, and mixtures, without being limited thereto.

As an example, aluminum is deposited on a silicon wafer using an e-beam evaporator, and photoresist is patterned on the aluminum using a photolithography technique. Thereafter, the aluminum is etched using the photoresist as a mask, the photoresist is removed, the silicon wafer is etched by deep ion reactive etching (DRIE) using the aluminum as a mask, the aluminum is removed, glass is anodically bonded onto the wafer and hermetically sealed, thereby fabricating the microchannels.

The microchannel has an average diameter of 80 to 120 μm, preferably 100 μm, without being limited thereto. If the average diameter of the microchannel is 80 μm or less, small sustained-release particles with a diameter of less than 40 μm may be produced, which may affect the release and in vivo absorption of the effective drug. In addition, if the produced sustained-release particles have a size of more than 100 μm, foreign body sensation and pain may increase when the particles are administered by injection, and the particle size distribution of the produced particles may increase, making it difficult to produce sustained-release particles having a uniform particle size distribution.

However, the average diameter of the microchannel may change depending on the pressure under which the first mixture and the second mixture are injected. In addition, the average diameter of the microchannel is closely related to the average diameter of the particles, but is also closely related to the pressure under which the first mixture and the second mixture are injected.

In addition, the cross-sectional width (w) and cross-sectional height (d) of the microchannel are closely related to the average diameter (d') of the produced sustained-release particles. Specifically, the cross-sectional width (w) of the microchannel is in the ratio range of 0.7 to 1.3 with respect to the average diameter (d') of the sustained-release particles, and the cross-sectional height (d) of the microchannel is in the ratio range of 0.7 to 1.3 with respect to the average diameter (d') of the sustained-release particles.

That is, when the average diameter (d') of the sustained-release particles to be produced is determined, it is possible to produce sustained-release particles having a desired size only when the cross-sectional width (w) and height (d) of the microchannel are set to the ratio range of 0.7 to 1.3 with respect to d'.

Step 3) is a step of injecting the first mixture and the second mixture into a first microchannel and a second microchannel, respectively, which have an intersection formed therebetween, and allowing the first mixture and the second mixture to flow under pressure.

That is, the first mixture flows along the first microchannel, and the second mixture flows along the second microchannel configured to form an intersection with the first microchannel, and meets the flow of the first mixture.

More specifically, the first mixture may be injected into the first microchannel under a pressure of 700 to 1,300 mbar, and the pressure may be increased at a first rate of 10 to 30 mbar/min, and when the pressure reaches 950 to 1,500 mbar, it may be increased at a second rate of 2 to 8 mbar/min.

In addition, the second mixture may be injected into the second microchannel under a pressure which is 2 to 4 times higher than the pressure under which the first mixture is injected into the first microchannel.

Specifically, in the production method using the microchannel, when the flow rates of the first mixture and the second mixture flowing inside the microchannels were set to certain values using a flow meter and the pressure was measured through feedback control, it was confirmed that the pressure required for the first mixture to flow through the microchannel at a certain flow rate increased gradually over time.

Therefore, it is possible to minimize the flow rate variability by using a method of constantly increasing the pressure applied to the first mixture, and to prevent the problem of non-uniform microparticle distribution or channel closure due to slow curing of the first mixture inside the microchannel, and to increase the production yield of desired microparticles.

In addition, the pressure conditions used when injecting the first mixture and the second mixture into the microchannels serve to control the average diameter of the produced microparticles, and if the above-described range is not specifically satisfied, a problem may arise in that the size of the produced particles is not uniform, or the average diameter range of the microparticles of the present invention is not satisfied, or the value of Equation 1 above is not satisfied.

That is, in order to increase the flow rate of the second mixture, which forms an intersection with the flow of the first mixture, compared to the flow rate of the first mixture injected into the microchannel in a straight-line direction, the second mixture is allowed to flow under a higher pressure.

As described above, when the flow rates of the first mixture and the second mixture are made different from each other and the flow rate of the second mixture is increased compared to the flow rate of the first mixture, the second mixture having a relatively higher flow rate compresses the first mixture at the point where the flow of the first mixture and the flow of the second mixture meet each other, and in this case, due to repulsive force between the first mixture and the second mixture, the biodegradable polymer and leuprolide in the first mixture form spherical microparticles, and more specifically, form microparticles in which leuprolide is uniformly distributed in the spherical biodegradable polymer.

Step 4) is a step of collecting microparticles. In this step, the microparticles are collected in a bath containing the second mixture to prevent aggregation of initially produced microparticles.

Step 4) is performed using the second mixture prepared in step 2), that is, a mixed solution of the surfactant and water. Specifically, a portion of the second mixture prepared in step 2) is injected into the microchannel, and the other portion is transferred into the bath in step 4) and used to prevent aggregation of the collected microparticles.

Step 5) is a step of removing an organic solvent from the microparticles collected in the bath. In this step, an organic solvent present on the surfaces of the sustained-release microparticles is evaporated and removed by stirring the microparticles at a predetermined stirring speed at a predetermined temperature. Specifically, step 5) may include steps of: 5-1) subjecting the microparticles to first stirring at a speed of 100 to 300 rpm at 15 to 20° C. for 20 to 40 minutes; 5-2) subjecting the microparticles to second stirring at a speed of 100 to 300 rpm at 30 to 40° C. for 60 to 120 minutes; and 5-3) subjecting the microparticles to third stirring at a speed of 100 to 300 rpm at 40 to 45° C. for 4 to 8 hours.

The first and the second stirring step are performed at different stirring speeds at different temperatures for different stirring times.

As described above, step 5) is characterized in that the stirring temperature is higher in the second stirring step than in the first stirring step. As the stirring temperature is increased stepwise, it is possible to control the evaporation rate of the organic solvent present on the surfaces of the microparticles. That is, it is possible to slowly evaporate the organic solvent present on the surfaces of the microparticles, thereby producing microparticles having a smooth surface.

The temperature at which the first mixture and the second mixture flow through the microchannels is also 15 to 20° C., preferably 17° C. That is, after the first and second mixtures flow through the microchannels and microparticles are produced at an intersection therebetween, the collected microparticles are constantly maintained at a low temperature of 15 to 20° C. until they are stirred in the first stirring step. It is possible to produce and maintain spherical particles only when microparticles are maintained at low temperature during the production thereof. That is, if a low-temperature condition is not used, a problem arises in that it is difficult to produce particles having a uniform spherical shape.

Thereafter, in the second stirring step and the third stirring step, the temperature is increased gradually and the stirring time is increased so that the organic solvent present on the surfaces of the microparticles may be slowly evaporated, thereby minimizing the effect of the organic solvent on the surfaces of the microparticles by evaporation of the organic solvent from the surface. That is, if the organic solvent is rapidly evaporated, a problem may arise in that the surfaces of the microparticles are not smooth and become rough due to evaporation of the organic solvent. In order to prevent this problem, the evaporation rate of the organic solvent may be controlled by increasing the temperature gradually as described above and also increasing the stirring process time, and due to this control of the evaporation rate of the organic solvent, it is possible to control the surface roughness of the produced microparticles.

Lastly, step 6) is a step of washing and drying the microparticles. In this step, the microparticles from which the organic solvent on the surface has been completely removed by stirring are washed several times with sterile filtered purified water to remove the surfactant remaining on the microparticles, and then the microparticles are freeze-dried.

The microparticles finally produced are in a form in which leuprolide is uniformly distributed in microparticles composed of the spherical biodegradable polymer, and contain leuprolide and the biodegradable polymer at a weight ratio of 1:2 to 1:10.

The weight ratio between leuprolide and biodegradable polymer contained in the microparticles is the same as the weight ratio in the first mixture. Specifically, as the organic solvent is completely evaporated and removed from the produced microparticles, the produced microparticles may contain leuprolide and the biodegradable polymer at the same weight ratio as the weight ratio in the weight ratio in the first mixture.

An injectable composition containing microparticles containing leuprolide according to another embodiment of the present invention may contain: microparticles containing leuprolide; and a suspending solvent.

The injectable composition is in a form in which the microparticles are uniformly distributed in the suspending solvent. When the injectable composition is administered, it may inject the microparticles themselves into the body, thereby exhibit the same effect as the effect of long-term administration of leuprolide.

More specifically, when the microparticles are injected into the body, the effect of releasing leuprolide by degradation of the biodegradable polymer may appear, and at this time, the microparticles of the present invention may exhibit the same effect as the effect of administering a certain concentration of leuprolide over a long period of time because they are in a form in which the biodegradable polymer and leuprolide are uniformly mixed.

That is, when the injectable composition of the present invention is injected once, leuprolide may be released in the body sustainably over a one month or more, and thus it is possible to improve the convenience of the user by solving the problem of having to take leuprolide every day. More specifically, when the injectable composition of the present invention is used, it is possible to provide a long-acting formulation in which leuprolide may be released sustainably for 1 month, a long-acting formulation in which leuprolide may be released sustainably for 3 months, or a long-acting formulation in which leuprolide may be released sustainably for 6 months.

The suspending agent contains an isotonic agent, a suspending agent, and a solvent.

More specifically, the isotonic agent may be selected from the group consisting of D-mannitol, maltitol, sorbitol, lactitol, xylitol, sodium chloride, and mixtures thereof, with D-mannitol being preferred, but the isotonic agent is not limited to the above examples.

The suspending agent is selected from the group consisting of sodium carboxymethylcellulose, polysorbate 80, starch, starch derivatives, polyhydric alcohols, chitosan, chitosan derivatives, cellulose, cellulose derivatives, collagen, gelatin, hyaluronic acid (HA), alginic acid, algin, pectin, carrageenan, chondroitin, chondroitin sulfate, dextran, dextran sulfate, polylysine, titin, fibrin, agarose, fluran, xanthan gum, and mixtures thereof, with sodium carboxymethylcellulose and polysorbate 80 being preferred, but the suspending agent is not limited to the above examples.

As the solvent, water for injection may be used, and any solvent that may be used as water for injection may be used without limitation.

Production Example 1

Production of Microparticles Containing Leuprolide

An API solution was prepared by dissolving leuprolide acetate in dimethyl sulfoxide. A biodegradable polymer solution was prepared by dissolving poly(lactide-co-glycolide) (PLGA) in dichloromethane.

A first mixture was prepared by mixing the API solution and the biodegradable polymer solution. In this case, the weight ratio between leuprolide acetate and the biodegradable polymer in the first mixture was 1:5.

A second mixture containing 0.5 wt % of polyvinyl alcohol was prepared by mixing polyvinyl alcohol as a surfactant with water.

The first mixture and the second mixture were injected into microchannels formed on a silicon wafer and allowed to flow.

At this time, in order to allow the first mixture and the second mixture to flow at certain flow rates, the first mixture was allowed to flow under pressure conditions where the pressure was increased from 1,000 mbar to 1,200 mbar at a rate of 20 mbar per minute and then increased at a rate of 7 mbar per minute, and the second mixture was allowed to flow under a pressure of 3,000 mbar. The temperature was maintained at 17° C., and the stirring speed was maintained at 300 rpm.

Microparticles produced at the intersection between the flow of the first mixture and the flow of the second mixture were collected in a water tank containing the second mixture. The microparticles collected in the bath were subjected to first stirring at a speed of 300 rpm for 30 minutes at 17° C., and then subjected to second stirring at a speed of 400 rpm for 1 hour at an increased temperature of 38° C., and then subjected to third stirring at a speed of 500 rpm for 3 hours at an increased temperature of 45° C.

After completion of stirring, the microparticles were washed several times with sterile filtered purified water and freeze-dried, thereby producing microparticles.

Production Example 2

Microparticles were produced in the same manner as in Production Example 1, except that a biodegradable polymer mixture was prepared by dissolving poly(lactide-co-glycolide) (PLGA) and polylactide (PLA) as a biodegradable polymers at a weight ratio of 1.7 to 18.3 in dichloromethane.

Production Example 3

Microparticles were produced in the same manner as in Production Example 1, except that a biodegradable polymer solution was prepared by dissolving polylactide (PLA) as a biodegradable polymer in dichloromethane.

Thereafter, the microparticles of Production Example 1 and the microparticles of Production Example 3 were mixed together at a weight ratio of 1:3.

Production Example 4

The microparticles of Production Example 1 and the microparticles of Production Example 3 were mixed together at a weight ratio of 1:4.

Production Example 5

Microparticles were produced in the same manner as in Production Example 1, except that the weight ratio between leuprolide acetate and the biodegradable polymer in the first mixture was 1:4.

Production Example 6

Microparticles were produced in the same manner as in Production Example 1, except that the weight ratio between leuprolide acetate and the biodegradable polymer in the first mixture was 1:7.

Production Example 7

Microparticles were produced in the same manner as in Production Example 1, except that the weight ratio between leuprolide acetate and the biodegradable polymer in the first mixture was 1:2.

Comparative Example 1

As a comparative example, a commercially available Leuplin DPS Inj. (Korea Takeda Pharmaceutical Co., Ltd.) was used. Specific information on the Leuplin DPS Inj. is shown in Table 1 below.

TABLE 1

|  | Leuplin DPS Inj. (Korea Takeda Pharmaceutical Co., Ltd.) |
| --- | --- |
| Leuprolide acetate | 11.25 |
| PLA | 99.30 |
| D-mannitol | 19.45 |
| Total amount (mg) | 130.00 |
| API:polymer ratio | 1:8.827 |

The microparticles were prepared into injectable formulations using the suspending solvent shown in Table 2 below.

TABLE 2

| Content criteria | Purpose of mixing | Component name | Quantity | Unit |
| --- | --- | --- | --- | --- |
| 2.0 mL | Isotonic agent | D-mannitol | 100.0 | mg |
|  | Suspending agent | Soduim carboxymethylcellulose | 10.0 | mg |
|  | Suspending agent | Polysorbate 80 | 10.0 | mg |
|  | Solvent | Water for injection | Remainder |  |

Experimental Example 1

Examination of Appearance of Microparticles

In order to examine the appearances of the microparticles of the Production Examples and the Comparative Example, the appearances of the produced microparticles were examined through SEM photographs.

Figure 1:
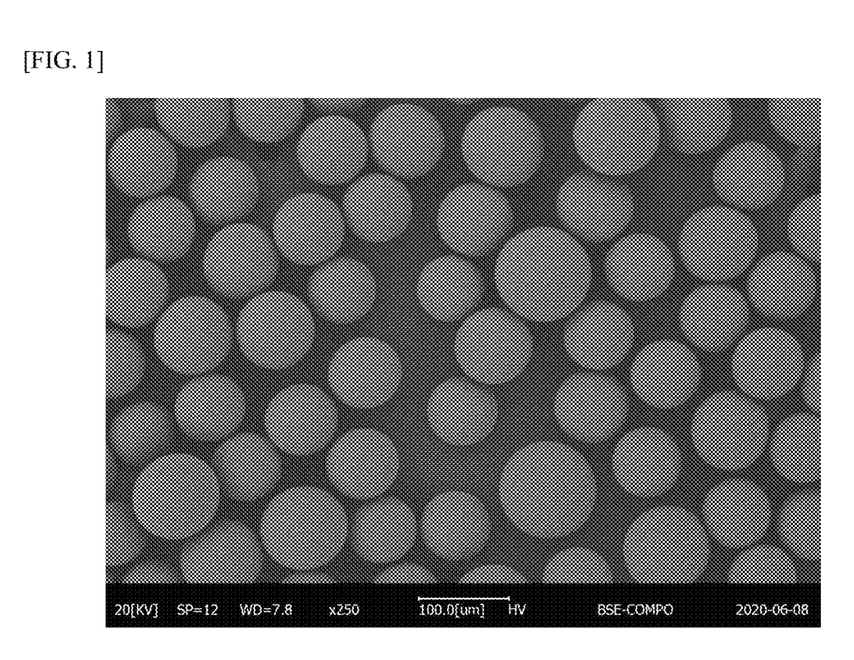
FIG. 1 is an SEM photograph of microparticles according to one example of the present invention.
Figure 2:
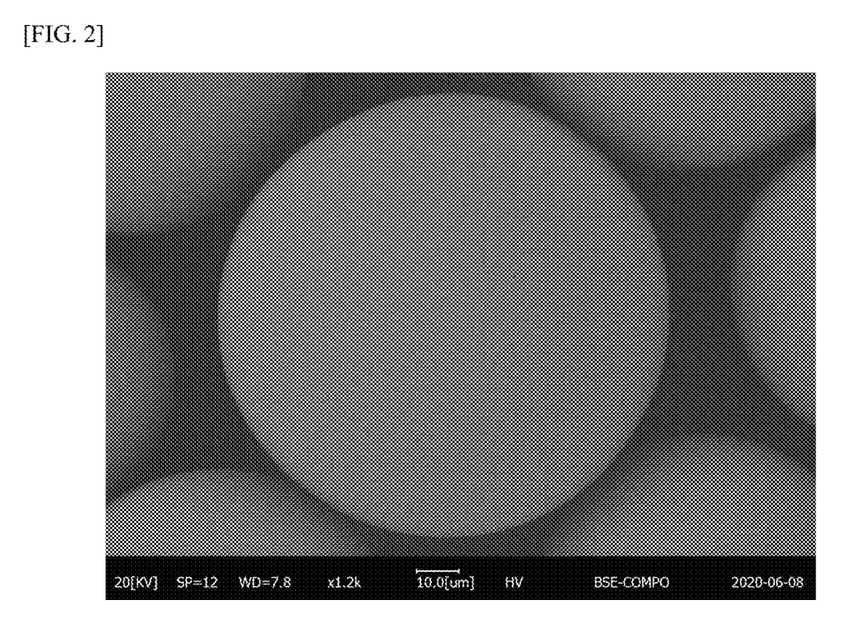
FIG. 2 is an SEM photograph of microparticles according to one example of the present invention.

FIGS. 1 and 2 show SEM photographs of the microparticles of Production Examples 1 to 7, and it can be confirmed that perfectly spherical sustained-release particles were produced.

Figure 3:
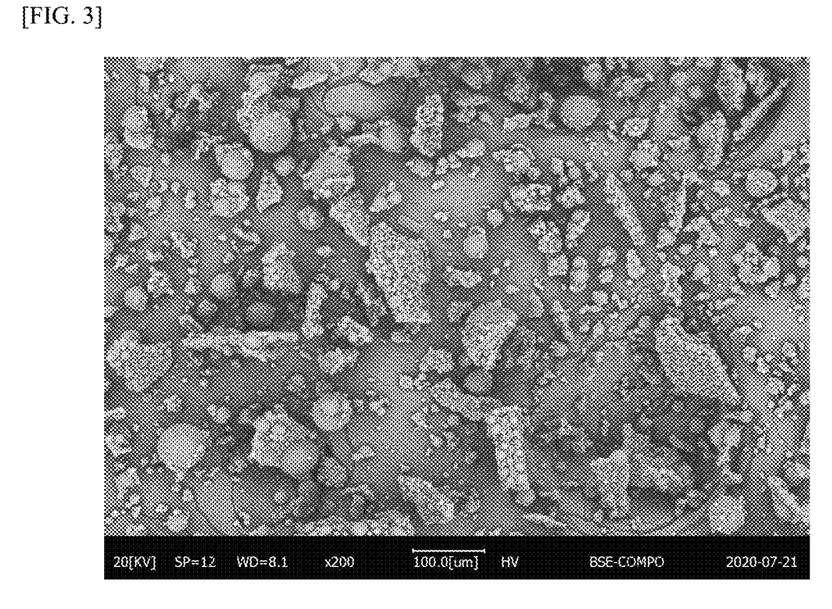
FIG. 3 is an SEM photograph of microparticles according to a comparative example.
Figure 4:
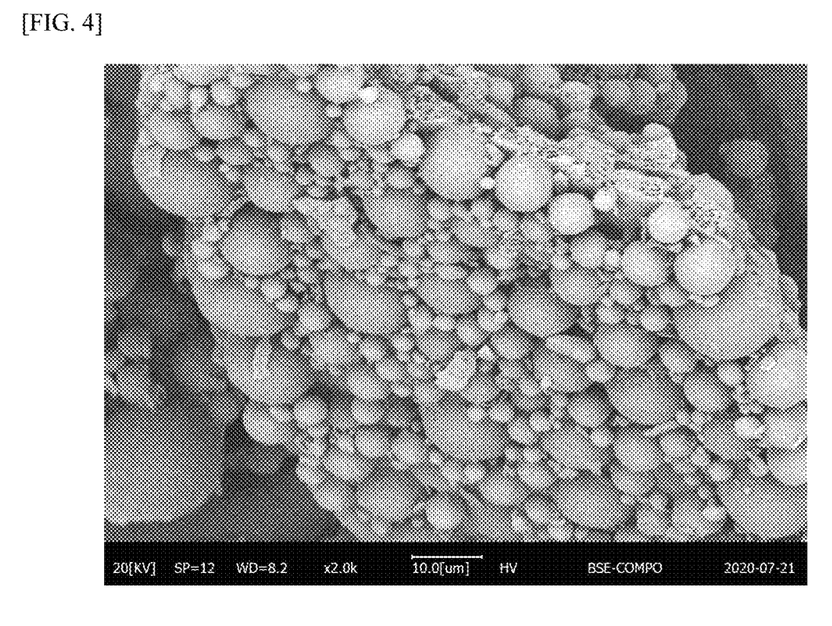
FIG. 4 is an SEM photograph of microparticles according to a comparative example.

FIGS. 3 and 4 are SEM photographs of Leuplin DPS Inj. of Comparative Example 1, and it can be confirmed that non-uniform particles are present in Leuplin DPS Inj.

In order to specifically examine the diameters of the microparticles, analysis for Production Example 1, Production Example 2 and Comparative Example 1 was performed using a Microtrac particle size analyzer.

TABLE 3

| Production Example 1 | | Production Example 2 | | Comparative Example 1 | |
| --- | --- | --- | --- | --- | --- |
| Percentile | Size (μm) | Percentile | Size (μm) | Percentile | Size (μm) |
| 10.00 | 55.29 | 10.00 | 72.26 | 10.00 | 5.88 |
| 20.00 | 57.56 | 20.00 | 75.28 | 20.00 | 9.23 |
| 30.00 | 59.57 | 30.00 | 77.38 | 30.00 | 12.20 |
| 40.00 | 61.46 | 40.00 | 79.18 | 40.00 | 15.71 |
| 50.00 | 63.29 | 50.00 | 80.99 | 50.00 | 19.21 |
| 60.00 | 65.10 | 60.00 | 82.85 | 60.00 | 23.67 |
| 70.00 | 66.98 | 70.00 | 84.84 | 70.00 | 28.88 |
| 80.00 | 69.06 | 80.00 | 87.23 | 80.00 | 35.15 |

TABLE 3-continued

| Production Example 1 | | Production Example 2 | | Comparative Example 1 | |
|---|---|---|---|---|---|
| Percentile | Size (μm) | Percentile | Size (μm) | Percentile | Size (μm) |
| 90.00 | 71.49 | 90.00 | 91.49 | 90.00 | 44.08 |
| 95.00 | 73.09 | 95.00 | 95.78 | 95.00 | 52.07 |
| $\dfrac{D90-D50}{D50-D10}$ | 1.025 | $\dfrac{D90-D50}{D50-D10}$ | 1.20 | $\dfrac{D90-D50}{D50-D10}$ | 1.87 |

Referring to Table 3 above, it can be confirmed that, in Comparative Example 1, the particle diameters of D10 to D95 are 5.88 μm to 52.07 μm, which correspond to a wide particle diameter distribution. As described above, for excessive release at an initial stage, Leuplin DPS Inj. of Comparative Example 1 is configured to contain microparticles having various sizes.

On the other hand, it can be confirmed that the microparticles of the present invention have uniform particle diameter distributions (55.29 μm to 73.09 μm for Production Example 1 and 72.26 μm to 95.78 μm for Production Example 2). In addition, it can be confirmed that the value determined by Equation 1 above is close to 1 for Production Example 1 and Production Example 2, but is greater than 1, suggesting that the particle size distribution of Comparative Example 1 is not uniform.

As other comparative examples, commercially available leuprolide formulations were purchased, and the appearance of the particles thereof was examined through SEM photographs.

Figure 5:
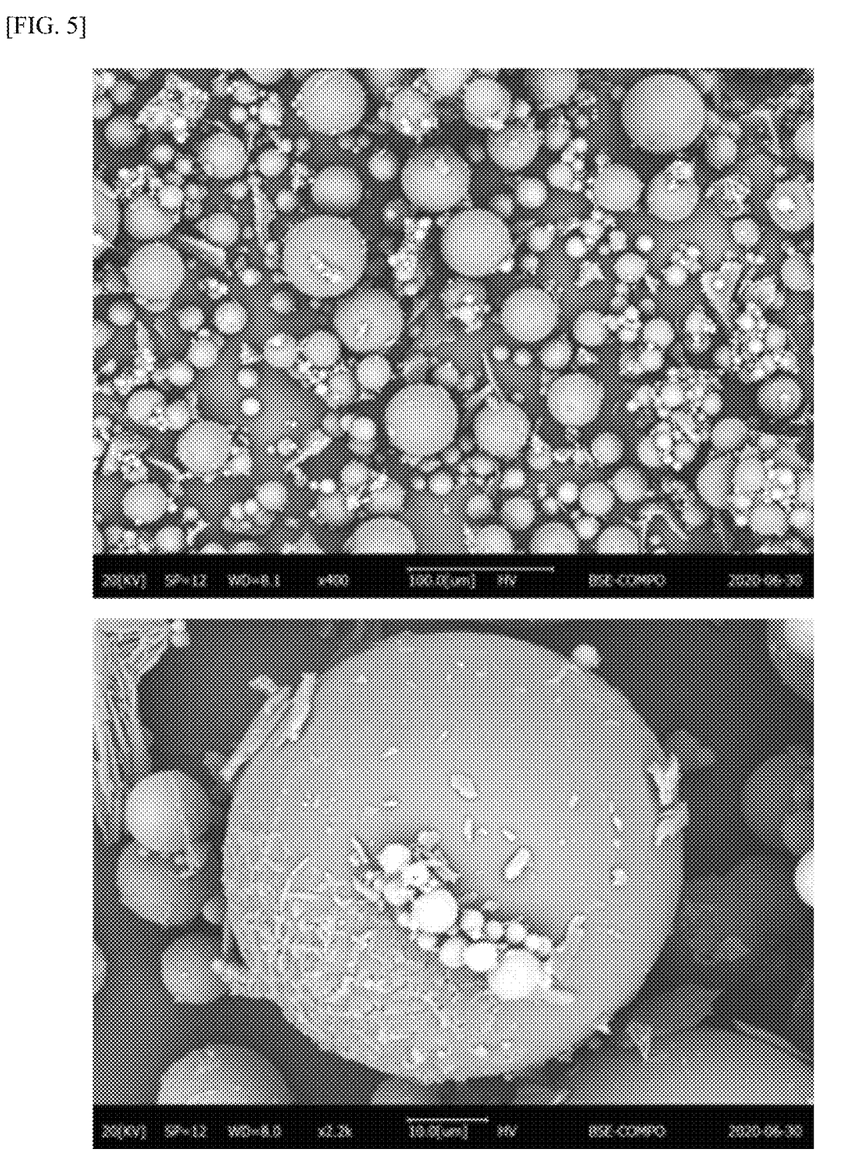
FIG. 5 is an SEM photograph of microparticles according to a comparative example.
Figure 6:
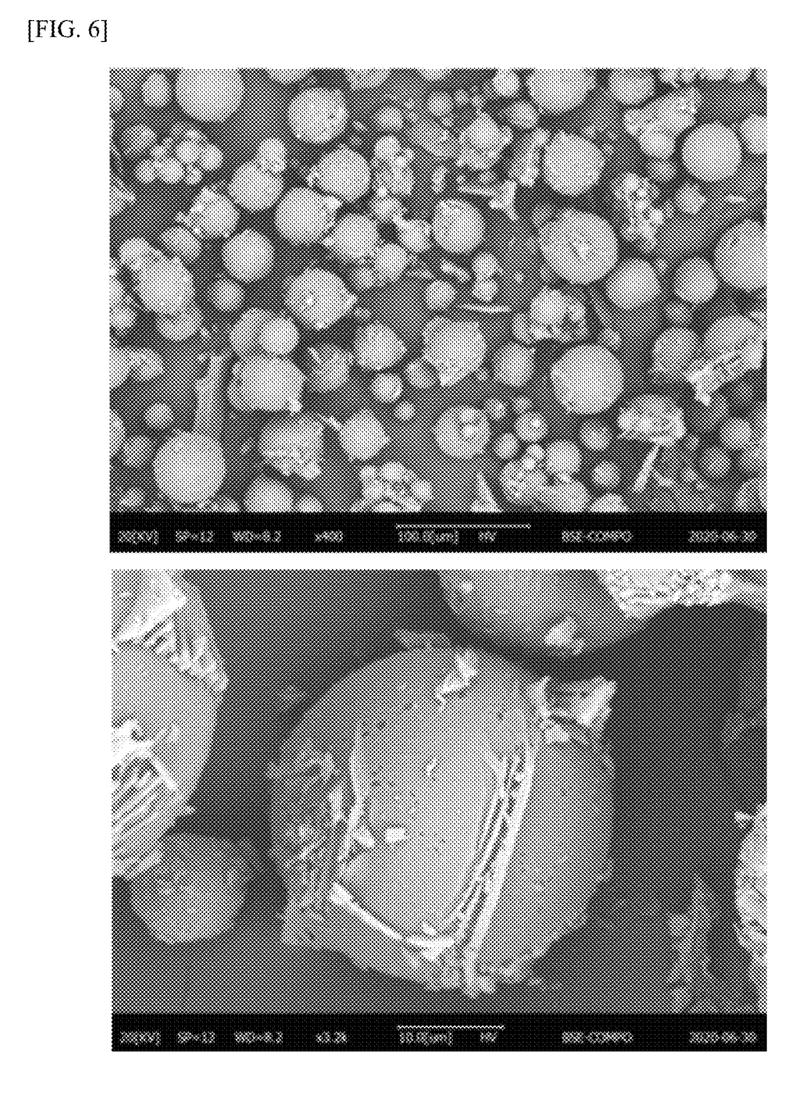
FIG. 6 is an SEM photograph of microparticles according to a comparative example.

FIG. 5 shows an SEM photograph of Lorelin Depot Inj. (Dongkook Pharmaceuticals Co., Ltd.), and FIG. 6 shows Luphere Depot Inj. (Daewoong Pharmaceutical Co., Ltd.).

Referring to FIGS. 5 and 6, it can be confirmed that, the particles have a non-uniform size and a broad size distribution, and that the surfaces of the particles are not smooth and are rough.

Experimental Example 2

Evaluation of Pharmacokinetic Characteristics

Pharmacokinetic evaluation of the microparticles containing leuprolide according to the present invention and an injectable formulation containing the same was performed.

The microparticles are a 1-month or longer sustained-release formulation, and examination was made as to whether the microparticles maintained the efficacy of leuprolide by releasing leuprolide sustainably over one month after injection.

Through the microparticles of the present invention, leuprolide acetate was administered to mice at a dose of 0.1 mg/kg.

In order to check the plasma concentration of leuprolide in the body, the microparticles were injected into 10 mice, and before 24 h, 18 h, 12 h, 6 h, 0 h before injection and 0.5 h, 1 h, 3 h, 6 h, 1 days, 2 days, 3 days, 4 days, 1 week, 2 weeks, 3 weeks and 4 weeks after administration to the mice by injection, the blood was collected and analyzed. The PK values shown in Table 3 below are the average PK values for 10 mice.

TABLE 3

| Time | TIME (hr) | PK Production Example 1 |
|---|---|---|
| | −24 | 0 |
| | −18 | 0 |
| | −12 | 0 |
| | −6 | 0 |
| | 0 | 0 |
| | 0.5 | 4.12 |
| | 1 | 13.32 |
| | 3 | 13.13 |
| | 6 | 8.76 |
| 1 day | 24 | 4.78 |
| 2 days | 48 | 1.92 |
| 3 days | 72 | 1.17 |
| 4 days | 96 | 0.86 |
| 1 week | 168 | 1.61 |
| 2 weeks | 336 | 2.09 |
| 3 weeks | 504 | 1.86 |
| 4 weeks | 672 | 1.68 |
| 5 weeks | 840 | 2.20 |
| $C_{max}/C_{24h}$ | | 2.79 |

In addition, in order to examine whether the drug is released sustainably over 3 months, an experiment was conducted in the same manner as described above, except that leuprolide acetate was administered to mice at an adjusted dose of 0.3 mg/kg through the microparticles which are a 3-month or longer sustained-release formulation of the present invention. An experiment on Comparative Example 1 was conducted in the same manner.

The results of the experiment are shown in Table 4 below.

TABLE 4

| Day | PK | |
|---|---|---|
| d | Production Example 2 | Comparative Example 1 |
| −1 | 0 | 0 |
| −0.75 | 0 | 0 |
| −0.5 | 0 | 0 |
| −0.25 | 0 | 0 |
| 0 | 0 | 0 |
| 0.01 | 346.813 | 4803.779 |
| 0.02 | 460.551 | 6660.572 |
| 0.04 | 486.102 | 7475.354 |
| 0.08 | 273.596 | 7589.883 |
| 0.13 | 128.908 | 5184.862 |
| 0.25 | 66.350 | 1287.771 |
| 0.5 | 148.698 | 643.497 |
| 1 | 87.603 | 401.335 |
| 2 | 55.667 | 44.172 |
| 3 | 35.895 | 22.934 |
| 4 | 34.396 | 21.015 |
| 7 | 21.016 | 10.414 |
| 14 | 6.501 | 14.327 |
| 21 | 5.358 | 16.114 |
| 28 | 5.993 | 17.985 |
| 42 | 23.749 | 22.018 |
| 56 | 93.315 | 28.323 |

TABLE 4-continued

| Day | PK | |
|---|---|---|
| d | Production Example 2 | Comparative Example 1 |
| 84 | 54.991 | 30.565 |
| 91 | 26.798 | 19.457 |
| $\dfrac{C_{max}}{C_{24h}}$ | 5.55 | 18.91 |

In Table 4 above, $C_{max}$ is the maximum plasma concentration of leuprolide for 24 hours after administration by injection, and $C_{24\,h}$ is the plasma concentration value of leuprolide in the blood collected 24 hours after administration by injection.

Referring to Tables 3 and 4 above, it can be confirmed that the microparticles of the present invention showed no excessive release at an initial stage in both the 1-month formulation and the 3-month formulation, and released leuprolide sustainably over 1 month or 3 months.

In addition, in the results of calculating the value of Equation 2 above, it can be confirmed that the value was 2.79 for the 1-month formulation and 5.55 for the 3-month formulation, which are included within the scope of the present invention, but the value was 18.91 for Comparative Example 1, which is out of the scope of the present invention.

In addition, it could be confirmed through the experiment that excessive release at an initial stage was larger in the Comparative Example 1 than in the Production Examples of the present invention.

Experimental Example 3

Evaluation of Pharmacokinetic Characteristics

Pharmacokinetic evaluation of the microparticles containing leuprolide according to the present invention and an injectable formulation containing the same was performed.

For evaluation, the formulations of each of Comparative Example 1 and Production Example 2 of the present invention was administered to beagle dogs, blood was collected from the beagle dogs, and the plasma concentration of leuprolide (PK) and the plasma concentration of testosterone (PD) were measured.

The injectable formulation containing the microparticles of Production Example 1 used as a 3-month or longer sustained-release formulation was 92.64 mg in total, and the content of leuprolide in the injectable formulation was 11.25 mg. Also, as Comparative Example 1, 11.25 mg Leuplin DPS Inj. was administered to each beagle dog.

For the experiment, each of Production Example 1 and Comparative Example 1 was administered to 5 beagle dogs by intravenous injection.

At 24 h, 18 h, 12 h, 6 h and 0 h before administration of each of Production Example 1 and Comparative Example 1 to the beagle dogs and 0 h, 0.25 h, 0.5 h, 1 h, 2 h, 3 h, 6 h, 12 h, 1 day, 2 days, 3 days, 4 days, 1 week, 2 weeks, 3 weeks, 4 weeks, 6 weeks, 8 weeks, 12 weeks, 13 weeks and 14 weeks after administration, the blood was collected and analyzed.

Figure 7:
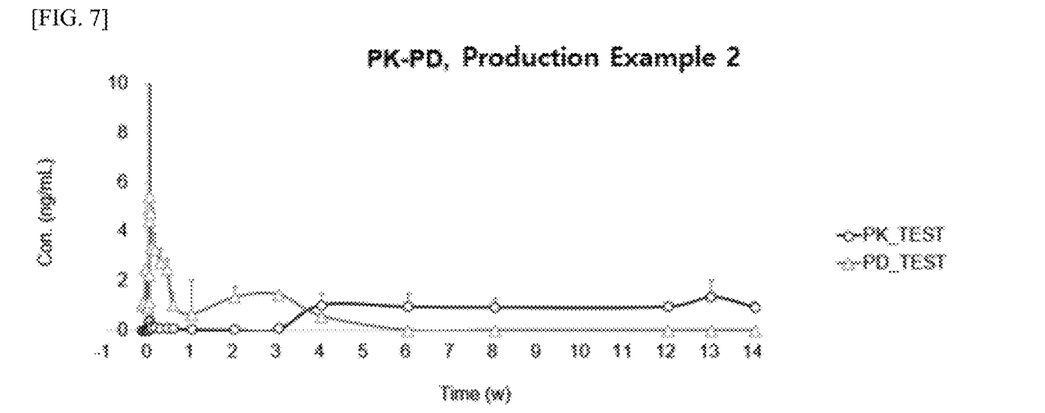
FIG. 7 shows PK-PD results obtained after administering microparticles according to one example of the present invention to beagle dogs by injection.
Figure 8:
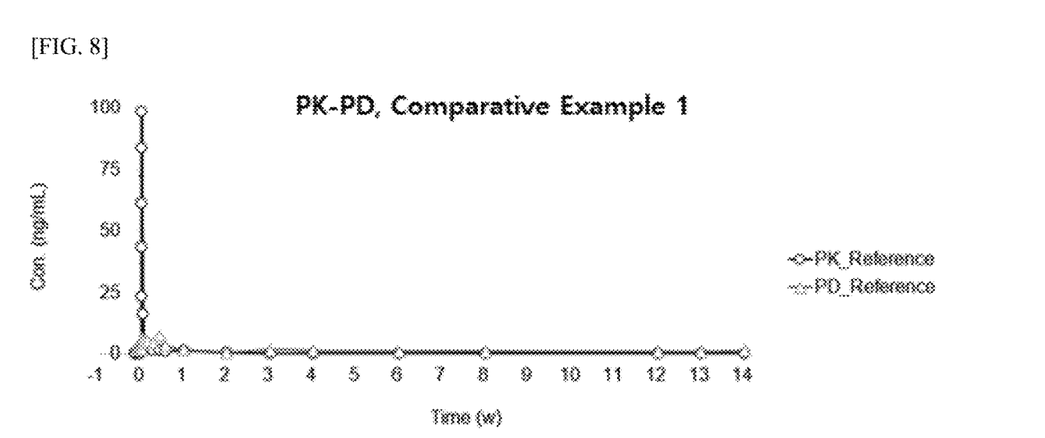
FIG. 8 shows PK-PD results obtained after administering microparticles according to one example of the present invention to beagle dogs by injection.

After blood collection, the average values of PK and PD for the five beagle dogs were calculated. The results of the calculation are shown in Table 5 below and FIGS. 7 to 9.

TABLE 5

| | | | PK | | PD | |
|---|---|---|---|---|---|---|
| Time (w) | Time (d, w) | Time (h) | Production Example 2 | Comparative Example 1 | Production Example 2 | Comparative Example 2 |
| −0.143 | | −24 | 0 | 0 | 1.014 | 1.378 |
| −0.107 | | −18 | 0 | 0 | 1.119 | 1.569 |
| −0.071 | | −12 | 0 | 0 | 2.450 | 2.924 |
| −0.036 | | −6 | 0 | 0 | 0.950 | 1.462 |
| 0.000 | | 0 | 0 | 0 | 0.913 | 3.017 |
| 0.001 | | 0.25 | 0.065 | 23.476 | 1.167 | 1.904 |
| 0.003 | | 0.5 | 0.205 | 43.535 | 2.252 | 4.078 |
| 0.006 | | 1 | 0.351 | 98.570 | 4.454 | 5.043 |
| 0.012 | | 2 | 0.407 | 83.505 | 4.972 | 6.029 |
| 0.018 | | 3 | 0.365 | 61.216 | 5.406 | 6.271 |
| 0.036 | | 6 | 0.187 | 16.511 | 4.752 | 6.119 |
| 0.071 | | 12 | 0.081 | 3.017 | 3.383 | 4.940 |
| 0.143 | 1d | 24 | 0.119 | 1.871 | 3.257 | 5.212 |
| 0.286 | 2d | 48 | 0.106 | 1.249 | 2.742 | 4.702 |
| 0.429 | 3d | 72 | 0.079 | 1.099 | 2.451 | 7.203 |
| 0.571 | 4d | 96 | 0.087 | 0.994 | 1.026 | 3.381 |
| 1 | 1w | 168 | 0.050 | 1.277 | 0.666 | 1.626 |
| 2 | 2w | 336 | 0.027 | 0.491 | 1.356 | 0.517 |
| 3 | 3w | 504 | 0.067 | 0.088 | 1.454 | 1.500 |
| 4 | 4w | 672 | 1.032 | 0.102 | 0.574 | 1.187 |
| 6 | 6w | 1008 | 0.953 | 0.086 | 0.005 | 1.035 |
| 8 | 8w | 1344 | 0.930 | 0.121 | 0 | 0.929 |
| 12 | 12w | 2016 | 0.958 | 0.133 | 0 | 0.799 |
| 13 | 13w | 2184 | 1.353 | 0.095 | 0 | 0.743 |
| 14 | 14w | 2352 | 0.941 | 0.092 | 0 | 1.143 |
| $\dfrac{C_{max}}{C_{24h}}$ | | | 3.42 | 52.68 | — | — |

In Table 5 above, $C_{max}$ is the maximum plasma concentration of leuprolide for 24 hours after administration by injection, and $C_{24\,h}$ is the plasma concentration value of leuprolide in the blood collected 24 hours after administration by injection.

From the results of PK measurement in the above experiment, it was confirmed that the maximum plasma concentration of leuprolide for 24 hours after administration by injection was 0.407 ng/ml for the injectable formulation containing the microparticles of the present invention, and was 98.570 ng/ml for Comparative Example 1, which significantly differs from that for the injectable formulation of the present invention. Accordingly, it was confirmed that the value determined by Equation 2 above was 3.42 for the injectable composition of the present invention, and was for 52.68 for Comparative Example 1, which significantly differs from that for the injectable formulation of the present invention.

In addition, from the results of PD measurement, it can be confirmed that the microparticles of the present invention showed a testosterone concentration of 0.5 ng/ml or less at 6 weeks after administration, suggesting that they exhibited a castration effect, whereas Comparative Example 1 did not show a testosterone concentration of 0.5 ng/ml or less, indicating that it did not exhibit an actual castration effect.

Figure 9:
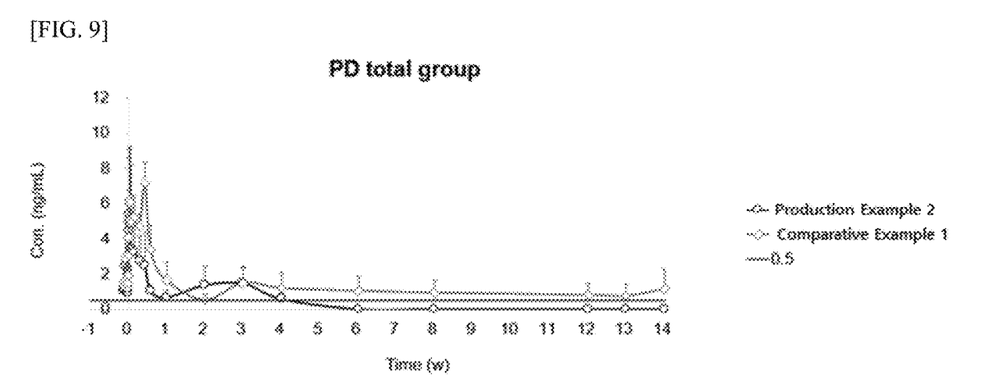
FIG. 9 shows PD results obtained after administering microparticles according to one example of the present invention to beagle dogs by injection.

More specifically, referring to FIG. 9 showing the results of measuring the PD value after administration of Production Example 2 and Comparative Example 1, it can be confirmed that the PD value for Production Example 2 showed a testosterone concentration of 0.5 ng/ml or less after 5 weeks, suggesting that Production Example 2 exhibited the effect of leuprolide. However, as a result of measuring the plasma testosterone concentration for Comparative Example 1 over 14 weeks, it was confirmed that the plasma testosterone concentration was higher than 0.5 ng/ml, suggesting that Comparative Example 1 did not exhibit the effect of leuprolide.

Although the preferred embodiments of the present invention have been described in detail above, the scope of the present invention is not limited thereto, and various modifications and improvements made by those skilled in the art using the basic concept of the present invention as defined in the appended claims also fall within the scope of the present invention.

What is claimed is:

1. Microparticles containing leuprolide and a biodegradable polymer and having an average diameter of 40 to 100 μm and a value of 0.5 to 2 as determined by the following Equation 1:

$$\frac{D90 - D50}{D50 - D10} \qquad \text{[Equation 1]}$$

wherein D10 is a particle diameter corresponding to 10% cumulative (from 0 to 100%) undersize particle size distribution, D50 is a particle diameter corresponding to 50% cumulative (from 0 to 100%) undersize particle size distribution, and D90 is a particle diameter corresponding to 90% cumulative (from 0 to 100%) undersize particle size distribution, wherein the leuprolide and the biodegradable polymer are contained in a weight ratio of 1:2 to 1:10.

2. The microparticles of claim 1, wherein, when the microparticles are administered by injection, a release rate of leuprolide at a target site is controlled, and thus a problem associated with excessive release of leuprolide at an initial stage is eliminated and a testosterone inhibitory effect of leuprolide lasts for one month or more.

3. The microparticles of claim 1, having a value of 1 to 15 as determined by the following Equation 2, which represents a plasma concentration of leuprolide measured after administering the microparticles containing leuprolide to a beagle dog by injection at a single dose of leuprolide acetate of 11.25 mg:

$$\frac{C_{max}}{C_{24h}} \qquad \text{[Equation 2]}$$

wherein $C_{max}$ is a maximum plasma concentration of leuprolide for 24 hours after administration by injection; and $C_{24\,h}$ is a plasma concentration value of leuprolide in blood collected 24 hours after administration by injection.

4. A method for producing microparticles containing leuprolide, the method comprising steps of:
1) preparing a first mixture by mixing leuprolide and a biodegradable polymer;
2) preparing a second mixture by dissolving a surfactant in a solvent;
3) injecting the first mixture and the second mixture into a first microchannel and a second microchannel, respectively, which have an intersection formed therebetween, and allowing the first mixture and the second mixture to flow, thereby producing microparticles at the intersection;
4) collecting the microparticles in a bath containing the second mixture;
5) removing an organic solvent from the collected microparticles; and
6) washing the microparticles, from which the organic solvent has been removed, with purified water, followed by freeze drying,
wherein the microparticles have a value of 0.5 to 2 as determined by the following Equation 1:

$$\frac{D90 - D50}{D50 - D10} \qquad \text{[Equation 1]}$$

wherein D10 is a particle diameter corresponding to 10% cumulative (from 0 to 100%) undersize particle size distribution, D50 is a particle diameter corresponding to 50% cumulative (from 0 to 100%) undersize particle size distribution, and D90 is a particle diameter corresponding to 90% cumulative (from 0 to 100%) undersize particle size distribution.

5. The method of claim 4, wherein the first mixture is injected into the first microchannel under a pressure of 700 to 1,300 mbar, and then the pressure is increased at a first rate of 10 to 30 mbar/min, and when the pressure reaches 950 to 1,500 mbar, the pressure is increased at a second rate of 2 to 8 mbar/min.

6. The method of claim 4, wherein the second mixture is injected into the second microchannel under a pressure which is 2 to 4 times higher than the pressure under which the first mixture is injected into the first microchannel.

7. The method of claim 4, wherein step 5) comprises steps of:
- 5-1) subjecting the microparticles to first stirring at a speed of 100 to 300 rpm at 15 to 20° C. for 20 to 40 minutes;
- 5-2) subjecting the microparticles to second stirring at a speed of 100 to 300 rpm at 30 to 40° C. for 60 to 120 minutes; and
- 5-3) subjecting the microparticles to third stirring at a speed of 100 to 300 rpm at 40 to 45° C. for 4 to 8 hours.

\* \* \* \* \*